US011648192B2

(12) United States Patent
Arnold

(10) Patent No.: US 11,648,192 B2
(45) **Date of Patent: *May 16, 2023**

(54) ORAL COMPOSITIONS

(71) Applicant: Michael Arnold, Beverly Hills, CA (US)

(72) Inventor: Michael Arnold, Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/468,518

(22) Filed: Sep. 7, 2021

(65) Prior Publication Data

US 2022/0000738 A1 Jan. 6, 2022

Related U.S. Application Data

(63) Continuation of application No. 17/187,636, filed on Feb. 26, 2021, now Pat. No. 11,110,045, which is a continuation of application No. PCT/US2019/063557, filed on Nov. 27, 2019.

(51) Int. Cl.

| | |
|---|---|
| ***A61K 8/42*** | (2006.01) |
| ***A61K 8/02*** | (2006.01) |
| ***A61K 8/25*** | (2006.01) |
| ***A61K 8/362*** | (2006.01) |
| ***A61K 8/38*** | (2006.01) |
| ***A61K 8/73*** | (2006.01) |
| ***A61Q 11/00*** | (2006.01) |
| ***A23G 4/06*** | (2006.01) |
| ***A23G 4/20*** | (2006.01) |
| ***A61K 8/19*** | (2006.01) |
| ***A61K 8/365*** | (2006.01) |

(52) U.S. Cl.

CPC ................ *A61K 8/42* (2013.01); *A23G 4/062* (2013.01); *A23G 4/20* (2013.01); *A61K 8/0216* (2013.01); *A61K 8/19* (2013.01); *A61K 8/25* (2013.01); *A61K 8/362* (2013.01); *A61K 8/365* (2013.01); *A61K 8/38* (2013.01); *A61K 8/73* (2013.01); *A61Q 11/00* (2013.01); *A61K 2800/31* (2013.01); *A61K 2800/92* (2013.01)

(58) Field of Classification Search

CPC ... A61K 9/68; A61K 7/16; A61K 9/50; A61K 33/10; A51K 7/20; A61Q 11/00

USPC ...................................................... 424/48, 53

See application file for complete search history.

(56) References Cited

U.S. PATENT DOCUMENTS

| | | | |
|---|---|---|---|
| 3,538,230 A | 3/1969 | Pader et al. | |
| 3,862,307 A | 1/1975 | Di Giulio | |
| 4,340,583 A | 7/1982 | Wason | |
| 4,741,905 A | 5/1988 | Huzinec | |
| 5,500,207 A | 3/1996 | Goulet | |
| 5,645,428 A | 7/1997 | Yarborough | |
| 5,713,738 A | 2/1998 | Yarborough | |
| 5,824,291 A | 10/1998 | Howard | |
| 5,902,568 A | 5/1999 | Ryles et al. | |
| 6,416,744 B1 | 7/2002 | Robinson et al. | |
| 6,696,043 B2 | 2/2004 | Orlowski et al. | |
| 6,696,044 B2 | 2/2004 | Luo et al. | |
| 6,746,664 B2 | 6/2004 | Allred | |
| 2002/0076384 A1* | 6/2002 | Orlowski | A23G 4/064 424/53 |
| 2004/0101497 A1 | 5/2004 | Montgomery et al. | |
| 2006/0177383 A1 | 8/2006 | Gebreselassie et al. | |
| 2006/0210488 A1 | 9/2006 | Jakubowski | |
| 2006/0263476 A1 | 11/2006 | Jani et al. | |
| 2010/0034871 A1 | 2/2010 | Mikkelsen et al. | |
| 2011/0250150 A1 | 10/2011 | Pedersen et al. | |
| 2014/0105948 A1 | 4/2014 | Gebreselassie et al. | |

FOREIGN PATENT DOCUMENTS

| | | | | |
|---|---|---|---|---|
| CA | 2806731 A1 | 2/2012 | | |
| EP | 1685875 A1 | 8/2006 | | |
| EP | 1919462 B1 | 7/2018 | | |
| WO | WO97/12607 | * | 4/1997 | A61K 9/68 |
| WO | 02094033 A1 | 11/2002 | | |
| WO | 2002092027 A2 | 11/2002 | | |
| WO | 2006086061 A1 | 8/2006 | | |
| WO | 2012145611 A2 | 10/2012 | | |

OTHER PUBLICATIONS

International Search Report and Written Opinion for PCT/US2019/063557, dated Feb. 5, 2020, 20 pages.

Ballal, Raksha, et al., "Effect of Chewing Bicarbonate-containing sugar-free gum on the Salivary pH: An in vivo Study", International Journal of Clinical Pediatric Dentistry, Mar. 2016, 5 pages.

* cited by examiner

*Primary Examiner* — Walter E Webb

(74) *Attorney, Agent, or Firm* — Arentfox Schiff LLP

(57) ABSTRACT

A chewable composition for teeth-whitening comprising a first region and a second region separated by a barrier layer; the first region comprising carbamide peroxide having water content of about 2% or less, a wetting agent (e.g., glycerin), an anhydrous chewing gum base having water content of about 1% or less, an anhydrous fruit acid, and one or more gum additives; and the second region comprising a chewable composition comprising a gum base, a source of bicarbonate ion, and one or more gum additives. A kit comprising separate chewable compositions corresponding to the first and second regions, and methods for whitening teeth using the chewable composition are also provided.

16 Claims, No Drawings

ORAL COMPOSITIONS

CROSS-REFERENCE TO RELATED APPLICATIONS

This application is a continuation application of U.S. patent application Ser. No. 17/187,636, filed Feb. 26, 2021, which is a continuation of PCT/US2019/063557, filed on Nov. 27, 2019, the disclosure of both of which are incorporated herein by reference in their entirety.

FIELD

The present disclosure relates to novel oral care compositions and methods of their use for cosmetic as well as chemotherapeutic purposes. More particularly, the disclosure relates to chewing gums for teeth-whitening.

BACKGROUND OF THE INVENTION

Teeth whiteners, also known as teeth bleaching agents, are in widespread use as a cosmetic means to enhance appearance and to contribute to better oral health and hygiene in general. Among teeth whitening formulations, those containing oxidizing agents as active ingredients are preferred because of their fast action and superior efficacy. The most frequently employed oxidizer in teeth Whitening compositions is a peroxide, either in free form as hydrogen peroxide, or as a non-covalent adduct with urea. Such an adduct is known as carbamide peroxide (or urea hydrogen peroxide). It has been well established that the higher the concentration of peroxide, the faster the whitening effect is achieved. However, it is important to note that the higher the concentration of peroxide, the greater the risk of gum and teeth root sensitivity, which has proven a significant problem for at least 10-15% of the population. Also, the higher the concentration of peroxide in the teeth-whitener, the higher the probability that the teeth-whitener will not be stable or have suitable shelf life for commercialization.

In general, stability is in direct conflict with the purpose of the peroxide-based teeth whitening compositions, which is to achieve the best possible whitening in a reasonable length of time of contact with the tooth surface. To accomplish this, the peroxide moiety must be short-lived (on the order of seconds) in the mouth, decomposing into an "active oxygen moiety" which is the ultimate effective teeth whitening agent. The requirement for quick decomposition in the mouth to generate the active oxygen moiety is in conflict with the need for long shelf life necessary for commercialization. The greater the stabilization, the slower the reactivity of the peroxide moiety, and the less effective the teeth-whitening action.

To improve on the rate of teeth-bleaching action of shelf-stable peroxide-based teeth-whiteners in the mouth, "activators" have been developed. For example, activation by use of UV light has been taught by U.S. Pat. Nos. 5,713,738 and 5,645,428 to Yarborough. For hydrogen peroxide, which is known to decompose in alkaline media, basic compounds and alkaline systems have also been disclosed as activators for hydrogen peroxide teeth-whiteners. For example, Allred, U.S. Pat. No. 6,746,664 B2 describes a variety of alkaline activation systems for whitening teeth. These alkaline agents are provided as a separate component that, when admixed with the hydrogen peroxide composition, reduces the time for hydrogen peroxide to react. However, it is known professionally that many of these teeth-whitening gels and gels with alkaline activators cause extreme sensitivity to the hard and soft tissue. Hydrogen peroxide is known to decompose in the presence of alkaline media. It is believed that the more rapid bleaching of the teeth is a direct consequence of the action of "activator." These alkaline agents typically include pH modifiers, including metal carbonates, metal bicarbonates, phosphates, amines and others. It is important to note, that even though the pH is controlled at a safe level by the addition of an alkaline based "activator," effectiveness of these activators in enhancing teeth-whitening reactivity of a hydrogen peroxide teeth-whitener system is questionable since they have not been shown to be better than the corresponding non-activated hydrogen peroxide teeth-whitening compositions (typically gels or pastes). Further, it should be noted that no significant difference in activation or teeth-whitening benefits has been reported for any metal carbonates or metal bicarbonates. Typically, in the prior art, a metal carbonate salt such as calcium carbonate, is the preferred activating and pH buffering agent.

Traditional teeth-whitening compositions and devices can be classified in three groups based on the method of delivering the material to tooth surfaces. The first is whitening toothpastes in which bleaching agents are typically incorporated as an additional component in the toothpaste formulations. These have not proven to be effective. The second group contains formulations intended specifically for whitening teeth, usually in gel form, which are typically delivered to the tooth surface by fabricated trays. Such material may be administered under the control of a dental professional or designed for in-home use. These treatments can be considered as the most effective among commercial treatments. The third group includes products designed to be used without the need of a dental professional and can be referred to as "out-of-office" products. Examples include strips, sprays, teeth-wipes, pens, and chewing gum products. A subset of these out-of-office products includes convenience as a main factor distinguishing the products. A chewing gum that serves to whiten the teeth is the most convenient form of a teeth-whitener since it is easy to carry and travel with, discrete when it is used, and non-intrusive for typical social activities.

Chewing gum whitening products offer an attractive alternative to more cumbersome and time intensive whitening systems because they are substantially more user friendly. People find chewing gum pleasurable and are willing to chew gum for much longer periods of time than they typically wear trays or brush their teeth. Such a method of delivery offers whitening action without sacrifice of time or comfort.

In general, the common shortcomings of existing "out-of-office" peroxide-based teeth whitening devices, especially those based on hydrogen or carbamide peroxides, are the inherent instability and lack of teeth-whitening efficacy. The efficacy of known teeth-whitening devices, especially that of chewing gum compositions, deteriorates over time, particularly when exposed to elevated temperatures and humid conditions.

Anhydrous carbamide peroxide is the most effective form of hydrogen peroxide that can be used in chewing guns since it is available in a dry form and is relatively stable in an essentially the anhydrous state. However, carbamide peroxide is particularly prone to accelerated decomposition when in contact with water, with other ingredients common to chewing gums such as metal ions from the various particulate matter present in the gum compositions, and with alkaline agents (e.g., calcium carbonate) or other alkaline materials. Goulet, U.S. Pat. No. 5,500,207, teaches a chewing gum comprising carbamide peroxide as the active teeth-whitening agent and is a prime example of one such composition not suitable for commercialization due to the inherent short shelf-life of these unstabilized carbamide peroxide. Carbamide peroxide is prone to hydration and once carbamide peroxide becomes hydrated, even to a small degree, it begins to decompose. Since hydration happens readily, unstabilized carbamide peroxide gum compositions do not have the shelf-life required for commercial products.

With regard to additives that stabilize carbamide peroxides, the current understanding is that the use of stabilizing additives is counterproductive because incorporation of such materials negatively affects the product's Whitening efficacy. See, for example, Howard, U.S. Pat. No. 5,824,291, which discloses the use of divalent metal peroxides and an alkaline gum base. These compositions have not proven effective for commercialization, most likely due to the lack of whitening activity, and also to short shelf life, which is most likely a direct consequence of the absence of a barrier between the alkaline substance (activator) and the peroxide moiety (divalent metal peroxide). In stark contrast to Howard, Orlaowski, et. al. U.S. Pat. No. 6,696,043 teaches a divalent metal peroxide that is activated by fruit acid, but also where there is a barrier between the fruit acid and metal peroxide to keep the metal peroxide from having contact with the fruit acid activator. For activity, the fruit acid and metal peroxide must first make contact, then react together in an aqueous environment (saliva). Here, the peroxide is stabilized by a non-reactive metal carbonate, and even upon "activation" by the fruit acid, does not provide for an effective dosage of "active peroxide" to realize any appreciable teeth whitening.

Microencapsulation has also been employed to aid in the stabilization of carbamide peroxide in chewing gum compositions. Microencapsulation is typically used as a means to protect actives in vitamin and food compositions. In microencapsulation, a barrier material is used to keep water and other materials from contacting the active ingredient and causing unwanted decomposition reactions. For teeth-whiteners, the active agent is typically carbamide peroxide. Gebreselassie (WO/2012/145611) and WO 2006/086061 teach improved stability of carbamide peroxide in chewing gum compositions by use of microencapusation technologies. However, these technologies have not yet resulted in an effective teeth-whitening chewing gum.

The requirement of anhydrous conditions places an additional limitation on chewing gum compositions taught in the prior art. Since prior art peroxide containing teeth-whitening chewing gum compositions require rigorously anhydrous compositions, they cannot be "extruded," and require compression using a conventional tablet press to produce the chewing gum composition. These tableted chewing gum compositions suffer from poor mouth feel, since they typically do not have the pleasant characteristics of the well-accepted commercial chewing gum products, which are made by extrusion. All commercial chewing gum products in today's marketplace, having blended composition and different shapes, including sticks, coated compositions, etc., are extruded. Extruded gums are more desirable, as they have a much better "mouth-feel" and, thus, are the most popular chewing gums in the marketplace. It is the water content of the "extrudable" chewing gum compositions that gives rise to peroxide containing chewing gum's unsuitability for extrusion. This instability is most likely due to the increased amount of glycerin (or "polyol lubricant") present in the extruded gum formulations. Glycerin (and propylene glycol) is extremely hygroscopic and always contains some water. As a result, such "extrudable" teeth-whitening chewing gums comprising a peroxide source (carbamide peroxide, metal peroxide, etc.) are not stable, and therefore not commercially viable. This instability is due to decomposition of the carbamide peroxide upon contact with water internal to the chewing gum composition. As a result, extrudable chewing gum compositions for teeth-whitening comprising a peroxide source, and specifically carbamide peroxide, have not been realized commercially.

It is important to also note that the teeth-whitening chewing gum compositions of prior art have not been shown to have any appreciable teeth-whitening efficacy. At best, they may be used for maintenance of teeth whiteness or for breath-freshening, not as a primary teeth-whitening device.

Further, abrasives and surfactants, claimed to have teeth-whitening activity, have been described as a substitute for peroxide in chewing gums. For example, Lawlor, WO 02/092027 and Luo, U.S. Pat. No. 6,696,044 each teach a teeth-whitening gum that uses a surfactant as the active whitening agent. Robinson, U.S. Pat. No. 6,416,744, teaches a chewing gum with silica as an abrasive and the active agent for teeth-whitening. However, none of Lawlor, Luo and Robinson provides a composition with any noticeable teeth-whitening activity. Sodium bicarbonate also has been used as a whitening agent. For example, Raksha K Ballal et al. (Int. J. Clin. Pediatr. Dent. 2016; 9(1):35-38) teaches a gum made with sodium bicarbonate to control pH of the saliva. Teeth-whitening activity of sodium bicarbonate chewing gums is nominal at best since they do not function to chemically remove stains. There are no reports of any significant teeth whitening achieved using a chewing gum comprising chiefly sodium bicarbonate as the active teeth-whitening agent.

Of importance chemotherapeutically, Dr. Keyes (National Institutes of Health) discovered that the use of hydrogen peroxide and baking soda (sodium bicarbonate) is useful as preventative and remedial treatment for periodontal diseases. Others using his technique also noted a teeth-whitening effect. In fact, the whitening effects of hydrogen peroxide aqueous solutions were first reported by the periodontal community in the 1970s. The use of hydrogen peroxide and baking soda as an efficacious combination for teeth-whitening, however, has never been reported, even though the use has been theorized, taught, and practiced as remedy and for the prevention of gingival diseases. Further, based on the available knowledge, sodium bicarbonate is not regarded to be as good an activator as sodium carbonate or potassium carbonate, which are stronger alkaline buffering agents.

One major drawback of the use of oral compositions having hydrogen peroxide in combination with alkaline activating agents, and specifically with carbonate and bicarbonate salts such as baking soda (sodium bicarbonate), is the inherent incompatibility of these agents with hydrogen peroxide. Hydrogen peroxide decomposes quickly in the presence of bases. Sodium bicarbonate is such a base. Prior art teaching relating to a hydrogen peroxide source and alkaline activator do not require a barrier between the activator (e.g., bicarbonate ion) and peroxide and thus, the combination is unstable. Also, the strengths of the two actives in gum compositions taught in the prior art are too low for achieving any appreciable teeth whitening in one treatment, and most likely even in multiple treatments.

For a commercial product, it is preferable that the two actives (hydrogen peroxide and the activator) be separated. In other words, a suitable commercial product comprising hydrogen peroxide and alkaline activator preferably has at least two independent parts, separated by a barrier. To this end, Ryles, et. al, U.S. Pat. No. 5,902,568 teaches a teeth-whitening toothpaste—a bi-phasic foam—in which hydrogen peroxide and sodium bicarbonate are stored separately and applied on the toothbrush before use. However, although stable, this toothpaste has not been shown to have any appreciable teeth-whitening effect. The lack of teeth whitening efficacy is due to the low strengths of the two actives and also to the method of their application to the teeth. Brushing of the teeth with such two-part (or biphasic) composition allows for only a short exposure of the tooth surface to the teeth-bleaching composition, which is inadequate to affect significant teeth whitening.

Thus, even though sodium bicarbonate and hydrogen peroxide have been taught as teeth-whitener, both independently and as a combination, there has been no demonstration of significant improvement in teeth-whitening using products based on these teachings compared to products based on using hydrogen peroxide alone as the bleaching agent. That is, there is no evidence to date that sodium bicarbonate (or any other alkaline activating agent) increases the whitening efficacy of hydrogen peroxide teeth-whiteners. This is possibly due to one or more of: (1) concentrations of hydrogen peroxide and the alkaline activator, e.g., sodium bicarbonate or another alkaline activator used are too low; (2) the device used for applying the combination is not effective; (3) the incipient oral chemistry does not allow full expression of the chemical potential of the combination, and; (4) the time of exposure of the surfaces to the actives is insufficient. These shortcomings are the basis for the lack of efficacy of prior art teeth-whitening methods using hydrogen peroxide and an alkaline activator, including those using sodium bicarbonate as the activator.

The shortcomings of prior art teeth whitening chewing gum formulations may be summarized as follows: (A) The difficulty in formulating chewing gums having appreciable whitening activity and adequate shelf life due to the vulnerability of anhydrous peroxides, particularly carbamide peroxide, in the presence of common ingredients of chewing gum formulations; (B) The difficulty of making peroxide containing chewing gums that allows for extrusion during manufacturing and that also produces gums of adequate shelf life; (C) Technical difficulties associated with manufacturing teeth whitening chewing gums in two parts that mix in the mouth during mastication; and (D) The poor whitening effect of teeth-whitening chewing gums of the prior art, which renders them not applicable for primary teeth-whitening, but only as potentially useful for maintenance of teeth previously whitened by traditional teeth-whiteners.

There is a need for a teeth-whitening chewing gum composition that has appreciable whitening efficacy, stability (long shelf-life) in commercially packaged form, and consumer acceptable "mouth feel," i.e., a chewing gum that has enough oxidizing power to significantly whiten teeth in one treatment, that also has a shelf life suitable for commercialization. And, there is a need for a bone-fide teeth-whitener that does not cause sensitivity of the soft and hard tissues of the oral cavity unlike other teeth-whiteners comprising carbamide peroxide.

SUMMARY OF THE INVENTION

Stable chewable gum-based compositions comprising a peroxide are provided. The compositions have shelf life suitable for commercialization in the form of packaged goods. Stability is achieved by choosing anhydrous ingredients (peroxide, fruit acid, and gum base), compounding under dry conditions, and using high amounts of the fruit acid (0.5-8 wt % of the composition; 5-800 mg, based on composition weight of 1-10 g). Also provided are chewable compositions that are biphasic, wherein one phase comprises the fruit acid-stabilized peroxide chewing gum composition and the other phase comprises a composition comprising a gum base and a source of bicarbonate ion. The two phases may be provided as one gum in which the phases are separated by a barrier layer, or as two independent chewable compositions. The composition is activated by chewing the two phases at the same time. The compositions further include gum additives. In some embodiments, the peroxide containing composition is free of metal ions.

In one aspect, described herein is a chewable composition comprising an anhydrous chewing gum base having water content of about 1% by weight or less, an anhydrous fruit acid, a peroxide having water content of about 2% by weight or less, and gum additives. In some embodiments, the fruit acid has a water content of less than 1% by weight.

In another aspect, the chewable gum composition ("the peroxide composition or gum") further comprises glycerin or propylene glycol such that the gum is extrudable during manufacture.

In a further aspect, the chewable composition further comprises an abrasive material.

In yet another aspect, biphasic chewable compositions are provided which combine any of the above chewable compositions with another chewable composition that comprises a source of bicarbonate ion. In some embodiments, the source of bicarbonate ion is sodium bicarbonate.

Further, a teeth-whitening kit comprising a peroxide containing component (component A) separated from a component comprising a source of bicarbonate ion (component B) is also provided.

In addition, methods of whitening teeth using the above-described biphasic chewable composition are provided.

The above-described biphasic chewable compositions are useful in prevention and remediation of many symptoms of oral diseases such as periodontal disease, gingivitis, and halitosis, and maintenance of healthy gingiva and breath. As such, methods for prevention and remediation of the symptoms of these diseases are also provided.

Aspects of the invention will become readily apparent to those skilled in the art from the following detailed description, wherein only exemplary configurations of the teeth-whitening chewable compositions, kits comprising the compositions, and methods for teeth-whitening and prevention and remediation of symptoms of oral diseases using the compositions are described.

As will be realized, the invention includes other and different aspects of the disclosed teeth-whitening chewable compositions, kits comprising the compositions, and methods for teeth-whitening and prevention and remediation of symptoms of oral diseases using the compositions. Further, it will be realized that the various details presented throughout this disclosure are capable of modification in various other respects, all without departing from the spirit and scope of the invention. Accordingly, the detailed description and the Examples that follow are to be regarded as illustrative in nature and not as restrictive.

DETAILED DESCRIPTION OF THE INVENTION

Chewable compositions comprising a peroxide at levels effective for teeth-whitening and having shelf life suitable for a commercial packaged goods are described. All ingredients are essentially anhydrous. The amount of water (by weight) that may be present in the chewable compositions comprising peroxide is about 5% or less, preferably about 4% or less and more preferably about 2% or less. Teeth whitening efficacy is a function of the concentration of the peroxide. The amount of peroxide per dosage of the teeth whitening treatment of the present invention is about 10-500 mg, preferably about 20-400 mg, more preferably about 35-350 mg, and most preferably about 100-300 mg.

The peroxide may be selected from the following: hydrogen peroxide; peroxides generally of the first or second group of the periodic table including calcium peroxide, calcium carbonate peroxide, sodium carbonate peroxide, zinc peroxide, strontium peroxide, other oxygen radical generating agents; and preferably carbamide peroxide.

In the chewable compositions of the present disclosure, the peroxide is provided with an anhydrous fruit acid. The term "fruit acid" as used herein includes organic acids naturally occurring in any of the common fruits. As used herein, by "anhydrous fruit acid" is meant a fruit acid having water content of less than 1%. The preferred fruit acid comprises citric acid. Other fruit acids, including tartaric acid, malic acid, mandelic acid, adipic acid, fumaric acid, gluconic acid, lactic acid, succinic acid, oxalic acid, glycolic acid, and acetic acid may also be employed either exclusively, or in combination with other fruit acids. The present disclosure provides chewable compositions that are extrudable during manufacture. These compositions preferably contain a wetting agent, preferably glycerin. Other wetting agents that may be used include ethylene glycol, polyethylene glycol, propylene glycol, polypropylene glycol, fatty acid esters; sorbitol, and combinations or mixtures thereof. The wetting agent is present at about 0.5-5% based on the weight of the chewable composition.

Chewing gum base ("gum base") can have different compositions described in greater detail below. The amount of chewing gum base in the chewable compositions described herein is about 10%-50% relative to the weight of the composition.

The compositions include one or more gum additives in an amount sufficient to make up 100% of a given composition. The additives can be confectionary components such as flavoring agents and surfactants. Xylitol is a flavoring agent of choice and may be used in combination with sucralose or other non-saccharide or non-polyol sweeteners such as aspartame or saccharine to achieve the desired sweetening and flavoring effect. The amount of xylitol, or other polyols such as sorbitol, mannitol, maltitol, etc., that may be used is about 10-70%, more preferably about 15-55%, and most preferably from about 23-45% relative to the weight of the chewable composition. The amount of sucralose, or other artificial or natural intense sweetening agents such as aspartame, or saccharine (or others including Stevia extracts and other naturally occurring intense sweeteners) that may be used is about 0.05-2%, more preferably about 0.1%-1.5%, and most preferably from about 0.3-1.2% relative to the weight of the chewable composition. Gum additives are described in greater detail below.

In some embodiments, the composition is free of metal ions.

Activation of the peroxide can be achieved by bringing the peroxide in contact with a chemical activator. For a shelf-stable peroxide-based commercial teeth-whitening product, the activating chemical agent preferably does not contact the peroxide in any appreciable extent until activation is desired. A preferred way to achieve this objective is to provide two compositions, one comprising a peroxide composition in which the peroxide is stabilized using fruit acid, and the other comprising the activator, such that upon chewing, the two compositions (or gum or phases), mix and the peroxide reacts to form the active, but short-lived chemical species that, ultimately, is the active agent for the teeth-bleaching reactions that result in teeth-whitening.

The present disclosure also provides chewable compositions having two phases (biphasic compositions in which one phase (the "peroxide" phase), comprises the fruit acid-stabilized chewing gum composition comprising significant amounts of peroxide, and the other phase ("activator" phase) comprises a composition having an activator and a gum base. In some embodiments, the activator is a metal bicarbonate salt or a combination of metal bicarbonate salts. In some embodiments, the activator is a combination of metal carbonates and bicarbonates. Small amounts of metal carbonate salts (e.g., sodium or potassium carbonate) may be employed to help stabilize the bicarbonate gum composition. The amount of metal carbonate salt that may be used is about 0.001-1%, preferably about 0.01-0.1%, and more preferably from about 0.02-0.05% of the weight of the activator phase.

The amount of activator that may be used is about 5-65% and preferably about 5-30% based on the mass of the second chewable composition.

A preferred activator is bicarbonate ion and a preferred source of bicarbonate ion is sodium bicarbonate. Potassium bicarbonate, a mixture of potassium and sodium bicarbonates, as well as other metal bicarbonates may also be used.

The two phases are kept physically separated until they are chewed together. Chewing takes place for a period of time sufficient for completion of the reaction between the active agents of each phase.

A surprisingly high degree of teeth whitening was observed using the chewable teeth-whitening compositions described herein. Typically, in the art of teeth-whitening using peroxide, an activator is expected to increase Whitening efficacy by about 0%-25% relative to un-activated peroxide. In stark contrast, using the chewable gum compositions described herein, unexpectedly high teeth-whitening, on the order of 100-1000%, was observed (see Example 6).

It was also surprisingly observed that the use of a source of bicarbonate ions, preferably sodium bicarbonate, as the activator for teeth-whitening led to a significant reduction in sensitivity caused by peroxide. In these preferred embodiments, sodium bicarbonate is present between 300 mg and 400 mg and carbamide peroxide is present at between 200 mg and 300 mg.

In some embodiments, the weight of activator in the second chewable composition is at least three times the mass of the fruit acid used in the complementary chewable composition comprising fruit acid stabilized peroxide.

Generally, the amount of activator in an acceptable formulation of the present invention is an amount that is enough to maintain the pH of the saliva at near neutral or slightly basic during and immediately after chewing both gum compositions simultaneously.

Further, the present disclosure provides a multi-phasic tablet, which can be produced, for example, from a tablet press, common to the art of pharmaceutical manufacturing of tablets. Such a tablet comprises essentially the same ingredients in the same relative and absolute amounts as the above-described chewable compositions, with additional ingredients added to aid in the tableting process—but without a wetting agent. These ingredients include binders, lubricators, coating, etc. Since these ingredients are well known to the pharmaceutical manufacturing art, they are not described here. In a single tablet containing both active agents, peroxide and activator, the agents are provided in separate layers. The layers (phases) are separated from each other by a barrier layer, which may be any inert substance that provides physical separation of the two layers. The barrier layer, for example, may be an anhydrous chewable gum composition. Alternatively, it may be a wax. Materials suitable as barrier layers are described in greater detail below.

In another acceptable multiphase composition, the peroxide phase composition may be microencapsulated with an inert micro-membrane. Such membranes are commonly used in the art of food chemistry, for example, for providing vitamin and other active agents in food products to achieve desired shelf-life. Prior art (see, for example, Gebreselassie, WO/2012/145611, hereby incorporated by reference) teaches microencapsulated chewing gum compositions, with details described therein of acceptable microencapsulation technologies.

Chewable Composition

Chewable Composition Comprising Peroxide, Gum Base, and Fruit Acid

In one aspect, the present disclosure provides a chewable composition for teeth whitening, comprising an anhydrous chewing gum base having water content of about 1% or less, an anhydrous fruit acid, a peroxide having water content of about 2% or less, and one or more gum additives. The ratio of gum base:peroxide:fruit acid, in percent weight relative to the composition, is about 10-50:1-20:0.5-8. The one or more gum additives are present in an amount necessary to reach 100% of the weight of the composition. In some embodiments, the water content of the composition is about 2% or less. In some embodiments, the fruit acid is citric acid. In some embodiments, the peroxide is carbamide peroxide. In some embodiments, the mass of the composition is about 0.2 g to about 10 g.

As used herein, the term "about" means within ±10%, preferably 5%, and more preferably 1% of the given value.

Generally, the gum base constitutes between about 10-50 wt % (percent weight) of the chewable composition. In one embodiment, the gum base is preset at about 20-35 wt % of the chewable composition.

In some embodiments, peroxide is present at about 1-20 wt % of the chewable composition. Alternatively, peroxide may be present at about 4-20 wt %, at about 8-20 wt %, at about 12-20 wt %, at about 1-15 wt %, or at about 5-15% of the chewable composition.

In some embodiments, fruit acid is present at about 0.5-8 wt % of the chewable composition. Alternatively, fruit acid may be present at about 1-7 wt %, at about 2-7 wt %, at about 3-7 wt %, at about 1-6 wt %, at about 1-5 wt %, or at about 0.5-5 wt % of the chewable composition Chewable Composition Comprising a Peroxide, Gum Base, Fruit Acid, and a Wetting Agent In another aspect, the chewable composition comprises a wetting agent in addition to a peroxide, gum base, fruit acid, and gum additives. In some embodiments, the gum base, peroxide, and fruit acid are present in same ratio as in the above-described chewable composition comprising gum base, peroxide, and fruit acid. In some embodiments, the fruit acid is citric acid. In some embodiments, the peroxide is carbamide peroxide. In some embodiments, the wetting agent is glycerin.

In some embodiments, the ratio of wetting agent:gum base:peroxide:fruit acid, in percent weight relative to the composition, is about 0.5-5:10-50:1-20:0.5-8. In some embodiments, the water content of the composition is about 2% or less. In some embodiments, the mass of the composition is about 0.2 g to about 10 g. In some embodiments, the ratio of wetting agent:gum base:peroxide:fruit acid in percent weight relative to the composition is about 1-3:20-35:5-15:0.5-8.

In some embodiments, the wetting agent is present at about 0.5-5 wt % of the chewable composition. Alternatively, the wetting agent may be present at about 1-5 wt %, at about 2-5%, at about 3-5 wt %, at about 1-4 wt %, or at about 2-4 wt % of the chewable composition.

Chewable Composition Comprising Peroxide, Gum Base, Fruit Acid, a Wetting Agent, and an Abrasive Material In another aspect, the present disclosure provides a chewable composition comprising an abrasive material in addition to peroxide, gum base, fruit acid, wetting agent, and one or more gum additives. In some embodiments, wetting agent, the gum base, peroxide, and the fruit acid are present in one or more of the same ratios as in the above-described chewable composition comprising wetting agent, gum base, peroxide, fruit acid, and gum additives. In some embodiments, the fruit acid is citric acid. In some embodiments, the peroxide is carbamide peroxide. In some embodiments, the wetting agent is glycerin.

In some embodiments, the ratio of the abrasive material: wetting agent:gum base:peroxide:fruit acid, in percent weight relative to the composition, is about 0.5-5:0.5-5:10-50:1-20:0.5-8.

In some embodiments, the abrasive material is present at about 0.5-5 wt % of the chewable composition. Alternatively, the abrasive material may be present at about 1-5 wt %, at about 2-5%, at about 3-5 wt %, at about 1-4 wt %, or at about 2-4 wt % of the chewable composition.

Biphasic Chewable Composition

Biphasic Chewable Composition Comprising Peroxide, Gum Base, Fruit Acid, and an Activator In another aspect, the present disclosure provides a chewable composition for teeth-whitening, comprising a first and a second region separated by a barrier layer.

The first region comprises the above-described chewable composition comprising peroxide, gum base, fruit acid, and one or more gum additives.

The second region comprises a chewable composition having an activator (or source thereof), a gum base, and one or more gum additives. The activator may comprise a source of bicarbonate ions.

The activator (or source thereof) and the gum base, respectively, are present in a ratio of about 5-30:15-50 in percent weight relative to the second region. The one or more gum additives are present in an amount necessary to reach 100% of the weight of the second region.

In some embodiments, the barrier layer comprises one or more components selected from the group consisting of lipids, proteins, carbohydrates, synthetic elastomers, polymers, wax, fat, and gum.

In some embodiments, the activator is bicarbonate ions and the source of bicarbonate ion is sodium bicarbonate.

In some embodiments, the second region further comprises a metal carbonate at about 0.001-1% of the weight of the second region.

In some embodiments, activator (or source thereof) is present at about 5-30 wt % of the second region. Alternatively, the activator (or source thereof) may be present at about 10-30 wt %, at about 15-30 wt %, at about 20-30 wt %, at about 5-25 wt %, at about 5-20 wt %, at about 5-15 wt %, at about 10-25 wt %, or at about 15-25 wt % the second region.

In some embodiments, the ratio of fruit acid:peroxide: activator, by mass, is about 0.5-5:5-30:15-45.

In some embodiments, the fruit acid is citric acid.

In some embodiments, the peroxide is carbamide peroxide.

In some embodiments, activator is present at three times or more the amount of the fruit acid.

Biphasic Chewable Composition Comprising a Wetting Agent, Peroxide Gum Base, Fruit Acid, an Activator In one aspect, provided herein is another chewable composition for teeth-whitening, comprising a first and a second region separated by a barrier layer.

The first region comprises the above-described chewable composition comprising a wetting agent, peroxide, fruit acid, and one or more gum additives.

The second region comprises a chewable composition having an activator (or source thereof), a gum base, and one or more gum additives. The activator may be bicarbonate ions.

The activator (or source thereof) and the gum base, respectively, are present in a ratio of about 5-30:15-50 in percent weight relative to the second region. The one or more gum additives are present in an amount necessary to reach 100% of the weight of the second region.

In some embodiments, the barrier layer comprises one or more components selected from the group consisting of lipids, proteins, carbohydrates, synthetic elastomers, polymers, wax, fat, and gum.

In some embodiments, the activator is bicarbonate ions and the source of bicarbonate ion is sodium bicarbonate.

In some embodiments, the second region further comprises a metal carbonate at about 0.001-1% of the weight of the second region.

In some embodiments, the activator (or source thereof) is present at about 5-30 wt % of the second region. Alternatively, activator (or source thereof) may be present at about 10-30 wt %, at about 15-30 wt %, at about 20-30 wt %, at about 5-25 wt %, 5-20 wt %, 5-15 wt %, at about 10-25 wt %, or at about 15-25 wt % the second region.

In some embodiments, the ratio of fruit acid:peroxide: activator (or source of activator), by mass, is about 0.5-1.5: 3-7:5-10.

In some embodiments, the fruit acid is citric acid.

In some embodiments, the peroxide is carbamide peroxide.

In some embodiments, the activator (or source thereof) is present at three times or more the amount of the fruit acid.

Biphasic Chewable Composition Comprising, an Abrasive Material, a Wetting Agent, Peroxide, Gain Base, Fruit Acid, and an Activator or Source of an Activator In yet another aspect, the present disclosure provides a chewable composition for teeth-whitening, comprising a first and a second region separated by a barrier layer.

The first region comprises the above-described chewable composition comprising an abrasive material, a wetting agent, peroxide, fruit acid, and one or more gum additives.

The second region comprises a chewable composition having an activator (or source thereof), a gum base, and one or more gum additives. The activator may be bicarbonate ions.

The activator (or source thereof) and the gum base, respectively, are present in a ratio of about 5-30:15-50 in percent weight relative to the second region. The one or more gum additives are present in an amount necessary to reach 100% of the weight of the second region.

In some embodiments, the barrier layer comprises one or more components selected from the group consisting of lipids, proteins, carbohydrates, synthetic elastomers, polymers, wax, fat, and gum.

In some embodiments, the activator is bicarbonate ions and the source of bicarbonate ions is sodium bicarbonate.

In some embodiments, the second region further comprises a metal carbonate at about 0.001-1% of the weight of the second region.

In some embodiments, activator (or source thereof) is present at about 5-30 wt % of the second region. Alternatively, activator (or source thereof) may be present at about 10-30 wt %, at about 15-30 wt %, at about 20-30 wt %, at about 5-25 wt %, at about 5-20 wt %, at about 5-15 wt %, at about 10-25 wt %, or at about 15-25% the second region.

In some embodiments, the ratio of fruit acid:peroxide: activator (or source thereof) by mass, is about 0.5-5:5-20: 10-35.

In some embodiments, the fruit acid is citric acid.

In some embodiments, the peroxide is carbamide peroxide.

In some embodiments, the activator (or source thereof) is present at three times or more the amount of the fruit acid.

Teeth-Whitening Kit

In one aspect, the present disclosure provides a teeth-whitening kit comprising a component A separated from component B. Component A comprises the chewable composition according to any of the above-described chewable composition comprising (1) peroxide, gum base, a fruit acid, and one or more gum additives; or (2) a wetting agent, peroxide, gum base, a fruit acid, and one or more gum additives; or (3) an abrasive material, a wetting agent, peroxide, gum base, a fruit acid, and one or more gum additives. Component B comprises a chewable composition comprising a gum base, an activator (or source thereof), and one or more gum additives. The one or more gum additives are present in an amount necessary to reach 100% of the weight of the second region.

In this kit, the ratio of the activator (or source thereof): gum base, in percent weight relative to component B, is about 5-30:15-50. The kit further includes instructions for use to achieve teeth-whitening.

In some embodiments, the activator is bicarbonate ions, and the source of bicarbonate ions is sodium bicarbonate.

In some embodiments, component B further comprises a metal carbonate at about 0.001-1% of the weight of component B.

In some embodiments, the relative amounts of component A and component B per dose of teeth-whitening treatment is such that activator (or source thereof) is present at three times or more the amount of the fruit acid.

In some embodiments, the ratio of fruit acid:peroxide: activator (or source thereof), by mass is about 0.5-5:5-20: 10-35.

In some embodiments, the fruit acid is citric acid.

In some embodiments, the peroxide is carbamide peroxide.

In some embodiments, the relative amounts of component A and component B per dose is such that pH of a water extract of the composition is at least about 7.

Teeth-Whitening Method

In one aspect, the present disclosure provides a method for whitening teeth in a human in need thereof. The method comprises placing in the oral cavity of the human a single composition according to any of the three above-described biphasic compositions; and chewing the composition for about 1 to about 30 minutes. The total weight of the composition is about 1 g to about 10 g and the chewing provides about 20 mg to about 400 mg hydrogen peroxide equivalents.

In some embodiments, the activator is bicarbonate ions and the source of bicarbonate ion is sodium bicarbonate. In some embodiments, the peroxide is carbamide peroxide.

In some embodiments, the second region of the single chewable composition further comprises a metal carbonate at about 0.001-1% of the weight of the second region.

In some embodiments, the ratio of fruit acid:peroxide: activator (source thereof), by mass is about 0.5-5:5-20:10-35.

In some embodiments, the fruit acid is citric acid.

In some embodiments, in the chewable composition, activator (source thereof) is present at three times or more the amount of the fruit acid.

In another aspect, the present disclosure provides another method for whitening teeth in a human in need thereof. The method comprises placing in the oral cavity of the human a first composition and a second composition; and chewing the compositions together for about 1 to about 30 minutes. The first chewable composition is one of the above-described chewable compositions comprising (1) peroxide, gum base, a fruit acid, and one or more gum additives; or (2) a wetting agent, peroxide, gum base, a fruit acid one or more gum additives; or (3) an abrasive material, a wetting agent, peroxide, gum base, a fruit acid, and one or more gum additives. The second composition comprises a chewable composition comprising a gum base, an activator (or source of an activator), and one or more additives. The one or more gum additives are present in an amount necessary to reach 100% of the weight of the second composition. The ratio of activator (or source thereof):gum base, in percent weight relative to the second composition is about 5-30:15-50. The total weight of the compositions is about 1 g to about 10 g and the chewing provides about 20 mg to about 400 mg hydrogen peroxide equivalents.

In some embodiments, the activator is bicarbonate ions and the source of bicarbonate ion is sodium bicarbonate.

In some embodiments, the second composition further comprises a metal carbonate at about 0.001-1% of the weight of the second composition.

In some embodiments, in the first and the second composition combined, the ratio of fruit acid:peroxide:activator (or source thereof), by mass is about 0.5-5:5-20:10-35. In some embodiments, the fruit acid is citric acid.

In some embodiments, the peroxide is carbamide peroxide.

In some embodiments, activator is present at three times or more the amount of the fruit acid.

In some embodiments, the pH of the saliva of the human during chewing is about 5.5 to about 7.

Remedial of Symptoms of Periodontal Disease

In one aspect, the present disclosure provides a method for remedial of periodontal disease in a human in need thereof, the method comprising: (a) placing in the oral cavity of the human a single chewable composition according to any of the three above-described biphasic compositions; and (b) chewing the composition for about 1 to about 30 minutes; wherein the total weight of the composition is about 1 g to about 10 g and the chewing provides about 20 mg to about 400 mg hydrogen peroxide equivalents.

In some embodiments, steps (a) and (b) are repeated. For example, the steps are performed one to five times a day for a period of 2-10 days. In some embodiments, the activator is bicarbonate ions and the source of bicarbonate ion is sodium bicarbonate. In some embodiments, the ratio of fruit acid:peroxide:activator (or source thereof), by mass is about 0.5-5:5-20:10-35. In some embodiments, the fruit acid is citric acid. In some embodiments the peroxide is carbamide peroxide. In some embodiments, in the chewable composition, the activator (or source thereof) is present at three times or more the amount of the fruit acid. In some embodiments, the pH of the saliva of the human during chewing is about 5.5 to about 7.

In another aspect, the present disclosure provides another method for remedial of periodontal disease in a human in need thereof. The method comprises (a) placing in the oral cavity of the human a first composition and a second composition; and (b) chewing the compositions together for about 1 to about 30 minutes. The first chewable composition is one of the above-described chewable compositions comprising (1) peroxide, gum base, a fruit acid, and one or more gum additives; or (2) a wetting agent, peroxide, gum base, a fruit acid one or more gum additives; or (3) an abrasive material, a wetting agent, peroxide, gum base, a fruit acid, and one or more gum additives. The second composition comprises a chewable composition comprising a gum base, an activator (or source thereof), and one or more additives. The one or more gum additives are present in an amount necessary to reach 100% of the weight of the second composition. The ratio of activator (or source thereof):gum base, in percent weight relative to the second composition is about 5-30:15-50. The total weight of the compositions is about 1 g to about 10 g and the chewing provides about 20 mg to about 400 mg hydrogen peroxide equivalents.

In some embodiments, steps (a) and (b) are repeated, for example the steps are performed one to five times a day for a period of 2-10 days. In some embodiments, the activator is bicarbonate ions and the source of bicarbonate ion is sodium bicarbonate. In some embodiments, the ratio of fruit acid:peroxide:activator (or source thereof), by mass is about 0.5-5:5-20:10-35. In some embodiments, the fruit acid is citric acid. In some embodiments the peroxide is carbamide peroxide. In some embodiments, in the chewable composition, the activator is present at three times or more the amount of the fruit acid. In some embodiments, the pH of the saliva of the human during chewing is about 5.5 to about 7.

Gum Base

Typically, the gum base contains elastomers (rubbers). The elastomers employed in the gum base will vary greatly depending upon various factors such as the type of gum base desired, the consistency of gum composition desired and the other components used in the composition to make the final chewing gum product. The elastomer may be any water-insoluble polymer known in the art and includes those gum polymers utilized for chewing gums and bubble gums. Illustrative examples of suitable polymers in gum bases include both natural and synthetic elastomers. For example, polymers which are suitable in gum base compositions include, without limitation, natural substances (of vegetable origin) such as chicle, natural rubber, crown gum, nispero, rosidinha, jelutong, perillo, niger gutta, tunu, balata, gutta-percha, lechi capsi, sorva, gutta kay, and the like, and combinations thereof. Examples of synthetic elastomers include, without limitation, styrene-butadiene copolymers (SBR), polyisbbutylene, isobutylene-isoprene copolymers, polyethylene, polyvinyl acetate and the like, and combinations thereof. A preferred gum base for use in the chewable compositions described herein is known by the tradename "NOVA-T" and is made by CAFOSA corporation. Another preferred gum base is "PIB-T" made by Eurobase.

Additional useful polymers include: crosslinked polyvinyl pyrrolidone, polymethylmethacrylate; copolymers of lactic acid, polyhydroxyalkanoates, plasticized ethylcellulose, polyvinyl acetatephthalate, and combinations thereof.

The amount of elastomer employed in the gum base may vary depending upon various factors such as the type of gum base used, the consistency of the gum composition desired and the other components used in the composition to make the final chewing gum product.

In some embodiments, the gum base may include wax. Wax softens the polymeric elastomer mixture and improves the elasticity of the gum base. When present, the wax(es) employed will have a melting point below about 60° C., and preferably between about 45° C. and about 55° C. The low melting wax may be a paraffin wax. The wax may be present in the gum base in an amount from about 6% to about 10%, and preferably from about 7% to about 9.5%, by weight of the gum base.

In addition to the low melting point waxes, waxes having a higher melting point may be used in the gum base in amounts up to about 5%, by weight of the gum base. Such high melting waxes include beeswax, vegetable wax, candelilla wax, carnuba wax, most petroleum waxes, and the like, and mixtures thereof.

In addition to the components set out above, the gum base may include a variety of other ingredients, such as components selected from elastomer solvents, emulsifiers, plasticizers, fillers, and mixtures thereof.

The gum base may contain elastomer solvents to aid in softening the elastomer component. Such elastomer solvents may include those elastomer solvents known in the art, for example, terpinene resins such as polymers of alpha-pinene or beta-pinene, methyl, glycerol and pentaerythritol esters of rosins and modified rosins and gums such as hydrogenated, dimerized and polymerized rosins, and mixtures thereof. Examples of elastomer solvents suitable for use herein include the pentaerythritol ester of partially hydrogenated wood and gum rosin, the pentaerythritol ester of wood and gum rosin, the glycerol ester of wood rosin, the glycerol ester of partially dimerized wood and gum rosin, the glycerol ester of polymerized wood and gum rosin, the glycerol ester of tall oil rosin, the glycerol ester of wood and gum rosin and the partially hydrogenated wood and gum rosin and the partially hydrogenated methyl ester of wood and rosin, and the like, and mixtures thereof. The elastomer solvent may be employed in the gum base in amounts from about 2% to about 15%, and preferably from about 7% to about 11%, by weight of the gum base.

The gum base may also include emulsifiers which aid in dispersing the immiscible components into a single stable system. The emulsifiers useful in this invention include glyceryl monostearate, lecithin, fatty acid monoglycerides, diglycerides, propylene glycol monostearate, and the like, and mixtures thereof. The emulsifier may be employed in amounts from about 2% to about 15%, and more specifically, from about 7% to about 11%, by weight of the gum base.

The gum base may also include plasticizers or softeners to provide a variety of desirable textures and consistency properties. Because of the low molecular weight of these ingredients, the plasticizers and softeners can penetrate the fundamental structure of the gum base making it plastic and less viscous. Useful plasticizers and softeners include lanolin, palmitic acid, oleic acid, stearic acid, sodium stearate, potassium stearate, glyceryl triacetate, glyceryl glyceryl monostearate, propylene glycol monostearate, acetylated monoglyceride, glycerine, and the like, and mixtures thereof. Waxes, for example, natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, propylene glycol, mixtures thereof, and the like, may also be incorporated into the gum base. The plasticizers and softeners are generally employed in the gum base in amounts up to about 20% by weight of the gum base, and more specifically in amounts from about 9% to about 17%, by weight of the gum base.

Plasticizers also include are the hydrogenated vegetable oils and include soybean oil and cottonseed oil Which may be employed alone or in combination. These plasticizers provide the gum base with good texture and soft chew characteristics. These plasticizers and softeners are generally employed in amounts from about 5% to about 14%, and more specifically in amounts from about 5% to about 13.5%, by weight of the gum base.

Anhydrous glycerin may also be employed as a softening agent, such as the commercially available United States Pharmacopeia (USP) grade. Glycerin is a syrupy liquid with a sweet warm taste and has a sweetness of about 60% of that of cane sugar. Because glycerin is hygroscopic, the anhydrous glycerin may be maintained under anhydrous conditions throughout the preparation of the chewing gum composition.

In some embodiments, the gum base of this invention may also include effective amounts of bulking agents such as mineral adjuvants which may serve as fillers and textural agents. Useful mineral adjuvants include calcium carbonate, magnesium carbonate, alumina, aluminum hydroxide, aluminum silicate, talc, tricalcium phosphate, dicalcium phosphate, calcium sulfate and the like, and mixtures thereof. These fillers or adjuvants may be used in the gum base compositions in various amounts. The amount of filler, may be present in an amount from about zero to about 40%, and more specifically from about zero to about 30%, by weight of the gum base. In some embodiments, the amount of filler will be from about zero to about 15%, more specifically from about 3% to about 11%.

A variety of traditional ingredients may be optionally included in the gum base in effective amounts such as coloring agents, antioxidants, preservatives, flavoring agents, and the like. For example, titanium dioxide and other dyes suitable for food, drug and cosmetic applications, known as F. D. & C. dyes, may be utilized. An anti-oxidant such as butylated hydroxytoluene (BHT), butylated hydroxyanisole (BFIA), propyl gallate, and mixtures thereof, may also be included. Other conventional chewing gum additives known to one having ordinary skill in the chewing gum art may also be used in the gum base.

Abrasive Material

Suitable abrasive materials include silicas, aluminas, phosphates, carbonates and combinations thereof. In some embodiments, the abrasive agent is a silica selected from: precipitated amorphous silica, silica gels, and combinations thereof. In some embodiments the abrasive material is selected from the following: calcium carbonate, sodium bicarbonate, sodium metaphosphate, potassium metaphosphate, tricalcium phosphate, dehydrated dicalcium phosphate, and combinations thereof.

The abrasive material contemplated for use in the chewable composition can be any material which does not excessively abrade dentin. However, silica dental abrasives have unique benefits of exceptional dental cleaning and polishing performance without unduly abrading tooth enamel or dentin. Silica is the preferred abrasive agent for the peroxide containing composition (or phase/layer) of the present invention. Other suitable abrasive materials, including aluminas, phosphates, carbonates and combinations thereof, may be employed as abrasive agents in the bicarbonate containing composition (or phase/layer) of the present invention.

The silica abrasive materials described herein, as well as other abrasive material, generally have an average particle size ranging between about 0.1 to about 30 microns, and preferably from about 5 to about 15 microns. The abrasive can be precipitated amorphous silica or silica gels such as the silica xerogels described in U.S. Pat. No. 3,538,230 to Pader, et al. and U.S. Pat. No. 3,862,307 to DiGiulio, both incorporated herein by reference in their entireties. Preferred are the silica xerogels marketed under the trade name "Syloid" by the W.R. Grace & Company, Davison Chemical Division. Also preferred are the precipitated amorphous silica materials, such as those marketed by the J.M. Huber Corporation under the trade name "Zeodent", particularly the silica carrying the designation "Zeodent 113". The types of silica dental abrasives useful in the present invention are described in detail in U.S. Pat. No. 4,340,583 to Wason, incorporated herein by reference in its entirety.

Gum Additives

Additives conventionally used in chewing gums are known to a person skilled in the art of manufacturing chewing gums and may be used in the compositions described herein. Such additives include bulk sweeteners, high intensity sweeteners, flavoring agents, softeners, emulsifiers, coloring agents, binding agents, acidulants, fillers, antioxidants, and other components such as pharmaceutically or biologically active substances, that confer desired properties to the finished chewing gum product.

Examples of suitable sweeteners are listed in the following. Suitable bulk sweeteners include e.g. both sugar and non-sugar components. Useful sugar sweeteners are saccharide-containing components commonly known in the chewing gum art including, but not limited to, sucrose, dextrose, maltose, dextrins, trehalose, D-tagatose, dried invert sugar, fructose, levulose, galactose, corn syrup solids, and the like, alone or in combination. Sorbitol can be used as a non-sugar sweetener. Other useful non-sugar sweeteners include, but are not limited to, other sugar alcohols such as mannitol, xylitol, hydrogenated starch hydrolysates, maltitol, isomaltol, erythritol, lactitol and the like, alone or in combination. High intensity artificial sweetening agents can also be used alone or in combination with the above sweeteners. Preferred high intensity sweeteners include, but are not limited to sucralose, aspartame, salts of acesulfame, alitame, saccharin and its salts, neotame, cyclamic acid and its salts, glycyrrhizin, dihydrochalcones, thaumatin, monellin, sterioside and the like, alone or in combination. In order to provide longer lasting sweetness and flavour perception, it may be desirable to encapsulate or otherwise control the release of at least a portion of the artificial sweetener. Techniques such as wet granulation, wax granulation, spray drying, spray chilling, fluid bed coating, coascervation, encapsulation in yeast cells and fibre extrusion may be used to achieve desired release characteristics. Encapsulation of sweetening agents can also be provided e.g. using as the encapsulation agent another chewing gum component such as a resinous compound.

If a low-calorie gum is desired, a low-caloric baking agent can be used. Examples of low caloric bulking agents include polydextrose, Raftilose, Raffilin, Inuline, fructooligosaccharides (NutraFlora®), palatinose oligosaccharided; guar gum hydrolysates (e.g. Sun Fiber®) or indigestible dextrins (e.g. Fibersol®). However, other low-calorie-bulking agents can be used.

Further chewing gum additives which may be included in the chewing gum mixture processed in the present process include surfactants and/or solubilizers. Anionic, cationic, amphoteric or non-ionic solubilizers can be used. Suitable solubilizers include lecithins, poly6xyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllatylate, sodium lauryl sulfate and sorbitan esters of fatty acids and polyoxyethylated hydrogenated castor oil (e.g. the product sold under the trade name CREMOPHOR), block copolymers of ethylene oxide and propylene oxide (e.g. products sold under trade names PLURONIC and POLOXAMER), polyoxyethylene fatty alcohol ethers, polyoxyethylene; sorbitan fatty acid esters, sorbitan esters of fatty acids and polyoxyethylene steraric acid esters.

Particularly suitable solubilizers include polyoxyethylene stearates, such as for instance polyoxyethylene(8)stearate and polyoxyethylene(40)stearate, the polyoxyethylene sorbitan fatty acid esters sold under the trade name TWEEN, for instance TWEEN 20 (monolaurate), TWEEN 80 (monooleate), TWEEN 40 (monopalmitate), TWEEN 60 (monostearate) or TWEEN 65 (tristearate), mono and diacetyl tartaric acid esters of mono and diglycerides of edible fatty acids, citric acid esters of mono and diglycerides of edible fatty acids, sodium stearoyllactylate, sodium laurylsulfate, polyoxyethylated hydrogenated castor oil, block-copolymers of ethylene oxide and propyleneoxide and polyoxyethylene fatty alcohol ether. The solubilizer may either be a single compound or a combination of several compounds.

Aroma agents and flavoring agents which are useful in the chewable compositions described herein include natural and synthetic flavorings in the form of freeze-dried natural vegetable components, essential oils, essences, extracts, powders, including acids and other substances capable of affecting the taste profile. Examples of liquid and powdered flavorings include coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

Various synthetic flavors, such as mixed fruit flavor may also be used. Sorbitol can be used as a non-sugar sweetener. Other useful non-sugar sweeteners include, but are not limited to, other sugar alcohols such as mannitol, xylitol, hydrogenated starch hydrolysates, maltitol, isomaltol, erythritol, lactitol and the like, alone or in combination.

Barrier Layer

The barrier layer in the chewable compositions of the present disclosure may include lipids, proteins, carbohydrates, synthetic elastomers, and combinations thereof. Synthetic elastomers may include, but are not limited to, styrene-butadiene copolymers (SBR), polyisobutylene, isobutylene-isoprene copolymers, polyethylene, polyvinyl acetate and combinations thereof. In some embodiments, the barrier layer has a thickness range of about 0.1 mm to about 1 cm.

The barrier layer may include a non-saccharide “candy” gum composition. The barrier layer may include a substantially continuous amorphous chewing gum candy matrix. Such a barrier layer has low porosity. A candy gum composition may be formed from a mixture of a melted gum base and a cooked hard “candy” syrup. In particular, in some embodiments, the candy gum composition is formed from a mixture of a melted chewing gum base and a cooked polyol. Such materials may normally contain from 0.1% to 5.0% water. The syrup component is to be prepared from non-fermentable sugars such as sorbitol, mannitol, xylitol, erythritol, lactitol and maltitol and syrups thereof, such as hydrogenated starch hydrolysates and sorbitol solutions. The amorphous polyols are useful for preparing an amorphous barrier layer with decreased porosity. Methods of preparing candy gum compositions suitable for use as the barrier layer compositions are described, for example, in U.S. Pat. No. 4,741,905, the entire contents of which are incorporated herein by reference.

In some embodiments the barrier layer is formed as a typical chewing gum composition having low water content, that comprises similar amounts of gum base and polyol sweetening and filling agent. Xylitol is the preferred polyol. In particular, a suitable barrier layer having low porosity may be prepared from a composition including at least 25-65% by weight of a gum base and about 25%-65% by weight of polyol. Fillers can include, for example, bulking agents (e.g., bulk sweeteners, mineral adjuvants, carriers and extenders), flavors and high intensity sweeteners.

In some embodiments the barrier layer is formed from a high gum base, low filler composition. In particular, a suitable barrier layer having low porosity may be prepared from a composition including at least 50% by weight of a gum base and less than 40% by weight of fillers. In some embodiments, the filler is present in the barrier layer in an amount of about 20 to about 40% by weight of the barrier layer. Fillers can include, for example, bulking agents (e.g., bulk sweeteners, mineral adjuvants, carriers and extenders), flavors and high intensity sweeteners. In some embodiments, the barrier layer is formed from a composition that includes less than 5% by weight of xylitol or other sugar alcohols and combinations thereof. In some other embodiments, the barrier layer composition includes no bulk sweeteners. Examples of high gum base, low finer gum compositions which are suitable for forming the barrier layer in the present invention are provided in International Publication Number WO 02/094033 A1, the entire contents of which are incorporated herein by reference.

The barrier layer may be formed from a hydrophobic substance. In some embodiments, the barrier layer is formed form at least one lipid, such as a fat or wax. Fats may include, for example, hydrogenated oils or saturated fatty acids. Waxes may include, for example, paraffin wax or beeswax.

In some other embodiments, the barrier layer may be formed from one or more hydrophilic biopolymers to serve as an effective barrier layer against these hydrophobic compounds. Examples of suitable hydrophilic barriers include, but are not limited to, gluten, milk proteins, gelatin, starch, pectinates and cellulose-ethers.

In other embodiments, the barrier layer may be formed from a combination of hydrophobic and hydrophilic substances. For example, lipids and biopolymers can be combined to form an effective barrier layer. Suitable biopolymers include, but are not limited to, proteins and polysaccharides. For example, these biopolymers include, but are not limited to, gluten, milk proteins, gelatin, starch, pectinates and cellulose-ethers. In some embodiments, a barrier layer formed from a combination of hydrophobic and hydrophilic substances may be an emulsion-based barrier layer.

In some embodiments, the barrier layer includes at least one gelling hydrocolloid. Hydrocolloids are hydrophilic polymers of vegetable, animal, microbial or synthetic origin that generally contain many hydroxyl groups and may be polyelectrolytes. Examples of gelling hydrocolloids which may be used in the barrier layer include, but are not limited to, agar, alginate, carrageenan, cellulose ethers, such as hydroxypropylmethyl cellulose and methylcellulose, gelatins, gellan gum, locust bean gum, pectin, starches, xanthan gum and combinations thereof.

Disclosure of suitable barrier layers may be found in the application US20060263476, which is hereby incorporated by reference.

EXAMPLES

Example 1

Discovery of Stability of Chewable Composition Comprising Carbamide Peroxide Using Fruit Acid as a Stabilizing Agent Sixteen different chewable compositions having different amounts of citric acid and carbamide peroxide were tested for stability. Combinations containing four different levels of citric acid (0%, 1%, 2%, and 5% relative to the weight of the composition), each combined with one of four different levels of carbamide peroxide (1.5%, 5.0%, 10.0%, 15.0% relative to the weight of the composition) were prepared. See Table 1 below, compositions A-P.

| Ingredient | Amount |
|---|---|
| Carbamide peroxide | variable (mg) |
| Gum base | 900 mg |
| Xylitol | variable (mg) |
| Spearmint oil (spray-dried) | 20 mg |
| Sucralose | 30 mg |
| Glycerin | 50 mg |
| Citric Acid | variable (mg) |
| Silica | 40 mg |

TABLE 1

Chewable compositions (2.0 g) having different concentrations of citric acid and carbamide peroxide

| | Peroxide gum | | | |
|---|---|---|---|---|
| Citric Acid (anhydrous) | 1.5% peroxide | 5% peroxide | 10% peroxide | 15% peroxide |
| 1% | A | D | G | J |
| 2% | B | E | H | K |
| 5% | C | F | I | L |
| 0% | M | N | O | P |

Other than the citric acid and the carbamide peroxide, each composition had the same composition. Any mass change due to change in mass of either citric acid or carbamide peroxide was compensated by the addition of xylitol. Stability was assessed by direct titration of hydrogen peroxide (starch iodide method), and also by as well as by subjective measurements of taste and visual characteristics. The samples were stored as packets scaled under argon in a temperature and humidity-controlled environment of 35° C. and 60% humidity. The results of stability assessment are shown in Table 2 below.

TABLE 2

Stability of peroxide gum as a function of citric acid concentration

| Citric Acid-Peroxide gum combination | % $H_2O_2$ 0 (days) | 30 (days) | 90 (days) | 180 (days) | 360 (days) |
|---|---|---|---|---|---|
| A | 0.5 | 0.4 | 0.3 | 0.2 | 0.7 |
| B | 0.5 | 0.5 | 0.5 | 0.5 | 0.4 |
| C | 0.5 | 0.5 | 0.5 | 0.5 | 0.4 |
| D | 1.6 | 1.4 | 1.2 | 1 | 0.9 |
| E | 1.6 | 1.6 | 1.6 | 1.5 | 1.4 |
| F | 1.6 | 1.6 | 1.6 | 1.6 | 1.5 |
| G | 3.3 | 2.9 | 7.8 | 2.7 | 2.5 |
| H | 3.3 | 3.3 | 3.2 | 3.1 | 3.1 |
| I | 3.3 | 3.3 | 3.2 | 3.2 | 3.1 |
| J | 5.2 | 4.9 | 4.5 | 4.4 | 3.2 |
| K | 5.2 | 5.1 | 5.1 | 5 | 4.9 |
| L | 5.2 | 5.1 | 5.1 | 5 | 5 |
| M | 0.5 | 0.3 | 0.2 | 0 | 0 |
| N | 1.6 | 1.1 | 0.6 | 0.1 | 0 |
| O | 3.3 | 2.4 | 1.8 | 0.9 | 0.1 |
| P | 5.2 | 4.1 | 2.1 | 0.9 | 0.3 |

The results show conclusively that of the sixteen combinations, eight, namely, B, C, E, F, H, I, K, and L demonstrated appreciable stability, i.e., demonstrated shelf life suitable for commercialization. Notably, each of these eight chewable gum composition compositions has citric acid > or =2%.

Example 2

Stable Carbamide Peroxide Gum Prepared by Tablet Press Technology

| Ingredient | Amount |
|---|---|
| Carbamide peroxide | 250 mg |
| Gum base | 900 mg |
| Xylitol | 850 mg |
| Sorbitol | 500 mg |
| Peppermint oil (spray-dried) | 25 mg |
| Sucralose | 30 mg |
| Citric Acid | 50 mg |
| Magnesium Stearate | 75 mg |
| Stearic Acid | 100 mg |
| Microcrystalline Cellulose | 125 mg |

The above-listed ingredients were combined and blended in a ribbon blender at slow speed until homogeneous, then submitted immediately to a tablet press. Circular tablets were ejected at about 2.6 grams per composition.

Example 3

Stable Carbamide Peroxide Chewable Gum Composition Prepared by Extrusion

The ingredients listed below, in the amounts shown, were used to produce chewable gum compositions by extrusion.

| Ingredient | Amount |
|---|---|
| Carbamide peroxide | 330 mg |
| Gum base ("PIB/NOVA-T") | 900 mg |
| Xylitol | 700 mg |
| Spearmint oil (spray-dried) | 20 mg |
| Sucralose | 30 mg |
| Citric Acid | 50 mg |
| Glycerin | 60 mg |
| Silica | 40 mg |

Example 4

Two Gum Composition Formulations for Maximum Teeth-Whitening

Thirty-two different combinations of carbamide peroxide containing chewable compositions, namely ("peroxide gum"), B, C, E, F, H, I, K, and L (see Example 1) and sodium bicarbonate containing chewable compositions ("bicarbonate gum") having the formulation shown below were tested for teeth-whitening efficacy.

Peroxide Containing Gum (Made by Extrusion)

| Ingredient | Amount |
|---|---|
| Carbamide peroxide | variable (mg) |
| Gum base ("PIB-T/NOVA-T") | 700 mg |
| Xylitol | variable (mg) |
| Spearmint oil (spray-dried) | 20 mg |
| Sucralose | 30 mg |
| Glycerin | 50 mg |
| Citric Acid | variable (mg) |
| Silica | 50 mg |

Procedure

1) Gum base and xylitol were added to a warm mixer and mixing started.

2) Upon softening of the resulting mixture, about half of the remaining xylitol was added and mixing continued for 2 minutes.

3) Citric acid, silicon dioxide, and carbamide peroxide were added and mixing continued for approximately 2 minutes.

4) Glycerin and coolant were added and mixing continued for approximately 1.5 minutes.

5) Remaining xylitol was gradually added and mixing continued for approximately 2 minutes.

6) Sucralose was added and mixing continued for approximately for 1 minute.

7) Flavor was added and mixing continued for 2-3 minutes until batch was uniform. Upon cooling, rectangular pieces, 2.0-2.2 g/piece, were extruded.

Bicarbonate Containing Gum (Made by Extrusion)

| Ingredient | Amount |
|---|---|
| Sodium bicarbonate | variable (mg) |
| Amorphous silica | 20 mg |
| Gum base ("PIB/NOVA-T") ( | 710 mg |
| Spray dried peppermint oil | 100 mg |
| Maltitol syrup | 250 mg |
| Xylitol | variable (mg) |

-continued

| Ingredient | Amount |
|---|---|
| Calcium carbonate | 5 mg |
| Sodium carbonate | 5 mg |
| Glycerol | 20 mg |
| Coating (xylitol) | 325 mg |
| Lecithin | 2 mg |
| Titanium dioxide | 5 mg |

* Xylitol was added in place of sodium bicarbonate, to achieve appropriate equal masses of the "bicarbonate" chewable gum composition Procedure 1) Gum base, xylitol, and titanium dioxide were added to a warm mixer and mixing started.
2) Upon softening of the resulting mixture, about half of the remaining xylitol was added and mixing continued for 2 minutes.
3) Coolant, sucralose, and sodium bicarbonate/silicon dioxide were added to the mixture and mixing continued for about 2 minutes.
4) Glycerin and remaining half of the maltitol syrup was added and mixing continued for about 1.5 minutes.
5) Remaining xylitol was gradually added and mixing continued for approximately 2 minutes.
6) Flavor was added and mixing continued for 2-3 minutes until batch was uniform. Upon cooling, rectangular pieces, 2.0-2.2 g/piece, were extruded.

Subjects chosen for the study had appreciably stained teeth (Vita Shade Guide, Classic, values >7, i.e., "darker" than "B4") and had not had teeth-whitening procedure performed for at least 3 years prior. The results, shown below in Table 3, conclusively showed that that six of the thirty two combinations demonstrated appreciable teeth-whitening.

TABLE 3

Teeth-whitening obtained using various carbamide peroxide bicarbonate gum compositions

| | Peroxide containing gum | | | | | | | |
|---|---|---|---|---|---|---|---|---|
| % BC | B | C | E | F | H | I | K | L |
| 5 | 0-1 | 0-1 | 0-1 | 0-1 | 1-1.5 | 1-1.5 | 1.5-2 | 1.5-2 |
| 10 | 0-1 | 0-1 | 0-1 | 0-1 | 1.5-2 | 1.5-2 | 2-2.5 | 2-2.5 |
| 15 | 0-1 | 0-1 | 1-1.5 | 1-1.5 | 3.5-5 | 2.5-3 | 3-3.5 | 3-3.5 |
| 0 | 0-1 | 0-1 | 0-1 | 0-1 | 0.5-1 | 1-1.5 | 1.0-1.5 | 1.0-1.5 |

% BC: % sodium bicarbonate in the bicarbonate containing gum

Compositions made with 15% sodium bicarbonate containing gum performed the best. More specifically, the best combination for teeth-whitening commercial product was found to be the combination of carbamide peroxide gum composition "H" with 15% bicarbonate containing gum composition as its complement. Without being limited by any theory or mechanism of action, it is believed that the most likely reason the "peroxide" gum composition "I" did not perform as well as the composition "H" is that with 5% citric acid, "I" has excess citric acid that reacts with the bicarbonate ion to reduce the effective amount of bicarbonate, leading to the pH of the oral cavity not being the most favorable to activate the peroxide moiety in-situ. See Table 1. Note that the composition "H" has 2% citric acid.

Also, some of the test subjects experienced slight discomfort when using the peroxide gum tablets having 15% carbamide peroxide (K, L), whereas no sensitivity was reported with the use of the 10% peroxide gums (H, I) when employed with its 15% bicarbonate gum complement. Notably, it was generally observed that the higher the amount of sodium bicarbonate with respect to the amount of carbamide peroxide, the lower was the observed tooth sensitivity.

Example 5

Two-Gum (Biphasic) Composition Made by Extrusion

The compositions of the peroxide gum and the bicarbonate gum of a exemplary two-gum (biphasic) composition is shown below.

Peroxide Gum

| Ingredient | Amount |
|---|---|
| Carbamide peroxide | 200 mg |
| Gum base | 660 mg |
| Xylitol | 900 |
| Spearmint oil (spray-dried) | 100 mg |
| Glycerin | 40 mg |
| Citric Acid | 50 mg |
| Sucralose | 15 mg |
| Amorphous silica | 50 mg |

Procedure

1) Gum base and xylitol were added to a warm mixer and mixing started.
2) Upon softening of the resulting mixture, about half of the remaining xylitol was added and mixing continued for 2 minutes.
3) Citric acid, silicon dioxide, and carbamide peroxide were added and mixing continued for approximately 2 minutes.
4) Glycerin and coolant were added and mixing continued for approximately 1.5 minutes.
5) Remaining xylitol was gradually added and mixing continued for approximately 2 minutes.
6) Sucralose was added and mixed for approximately 1 minute.
7) SD flavor was added and mixing continued for 2-3 minutes until batch was uniform. Upon cooling, rectangular pieces, 2.0-2.2 g/piece, were extruded.

Bicarbonate Gum

| Ingredient | Amount |
|---|---|
| Sodium bicarbonate | 300 mg |
| Amorphous silica | 30 mg |
| Gum base ("Nova-T/PIB-T") | 650 mg |
| Spray dried peppermint oil | 100 mg |
| Glycerin | 60 mg |
| Xylitol | 890 mg |
| Surfactant (SLS) | 5 mg |
| Calcium carbonate | 5 mg |
| Sodium carbonate | 5 mg |
| Sucralose | 60 mg |
| Titanium Dioxide | 5 mg |
| Lecithin | 3 mg |

Procedure

1) Gum base, xylitol, and titanium dioxide were added to a warm mixer and mixing started.
2) Upon softening of the resulting mixture, about half of the remaining xylitol was added and mixing continued for 2 minutes.
3) Coolant, sucralose, and sodium bicarbonate/silicon dioxide were added to the mixture and mixing continued for approximately 2 minutes.

4) Glycerin was added and mixing continued for approximately 1.5 minutes.
5) Remaining xylitol was gradually added and mixing continued for approximately 2 minutes.
6) Flavor was added and mixing continued for 2-3 minutes until batch was uniform. Upon cooling, rectangular pieces, 2.0-2.2 g/piece, were extruded.

Example 6

Demonstration of Synergistic Teeth-Whitening Activity with Simultaneous Use of the Peroxide Gum and the Bicarbonate Gum Improvement in teeth-whitening by biphasic gum (combination of peroxide gum and bicarbonate gum) was compared to the improvement in teeth-whitening achieved with the peroxide gun and the bicarbonate gum alone.

Twelve subjects were chosen, none ever having had their teeth bleached. Their teeth were heavily stained due to smoking. Subjects qualified for the study if they demonstrated whitening levels darker than "B4" grade using the Vita Shade Guide (Classic). The subjects used: (a) either a single peroxide gum prepared according to Example 4 (ca. 2 gram per piece), or; (b) a single bicarbonate gum prepared according to Example 4 (2 gram per piece), or; (c) the two gums together, chewed simultaneously. The gums were chewed for 30 minutes. The results of the chewing are shown in Table 4 below.

TABLE 4

Teeth-whitening efficacy of peroxide and bicarbonate gum combined compared to that of peroxide gum or bicarbonate gum

| Subject | Type of Gum<br>Peroxide Gum | <br>Bicarbonate Gum | <br>Peroxide Gum + Bicarbonate Gum |
|---|---|---|---|
| 1 | 0 | 0 | 3 |
| 2 | 0 | 0 | 2 |
| 3 | 1 | 0 | 4 |
| 4 | 0 | 0 | 4 |
| 5 | 1 | 0 | 5 |
| 6 | 0 | 0 | 2 |
| 7 | 0 | 0 | 3 |
| 8 | 1 | 0 | 4 |
| 9 | 1 | 1 | 4 |
| 10 | 1 | 0 | 3 |
| 11 | 1 | 1 | 5 |
| 12 | 1 | 1 | 4 |
| Average shade change in whitening | 0.58 | 0.25 | 3.58 |

The results show a dramatic increase in whitening observed for the peroxide gum due to the presence of the bicarbonate gum. A tenfold increase in whitening (1000% increase) was observed. Specifically, average whitening levels were observed to be very little (0.58 shade) if any, when the subject only used the "peroxide gum" (no "bicarbonate gum"). Likewise, when the subjects chewed only the "bicarbonate gum," no appreciable teeth-whitening took place. In stark contrast, when the two gums were chewed together, a shade change of between 2-5 shades was observed, with an average change of about 3.6 shades.

These data demonstrate a strong whitening effect when both gums are chewed together. The magnitude of the effect is much greater than would be expected from a teeth-whitener in general, and especially from a teeth-whitening gum. The effect is a result of sodium bicarbonate and carbamide peroxide being present together in an oral mixture. Further, the magnitude of the teeth-whitening effect is much greater than would be expected if sodium bicarbonate functioned solely by activating the peroxide by pH control.

Example 7

Single Composition Multi-Phasic Teeth Whitening Tablet

The three compositions below were compounded using a standard ribbon blender at low speed and pressed into a single multi-layered tablet, having the middle layer (of the three-layer tablet) as the barrier layer comprising anhydrous chewing gum base and no active.

Bicarbonate Layer (Phase)

| Ingredient | Amount |
|---|---|
| Sodium Bicarbonate | 375 mg |
| Amorphous Silica | 20 mg |
| Gum base | 800 mg |
| Spray dried peppermint oil | 100 mg |
| Xylitol | 700 mg |
| Calcium carbonate | 5 mg |
| Sodium carbonate | 5 mg |
| Magnesium Stearate | 80 mg |
| Stearic Acid | 125 mg |
| Microcrystalline Cellulose | 200 mg |
| Coating (xylitol) | 25 mg |

Peroxide Layer (Phase)

| Ingredient | Amount |
|---|---|
| Carbamide peroxide | 250 mg |
| Gum base | 900 mg |
| Xylitol | 850 mg |
| Sorbitol | 500 mg |
| Peppermint oil (spray-dried) | 25 mg |
| Sucralose | 30 mg |
| Citric Acid | 50 mg |
| Magnesium Stearate | 75 mg |
| Stearic Acid | 100 mg |
| Microcrystalline Cellulose | 125 mg |

Intermediary Barrier Layer (Phase)

| Ingredient | Amount |
|---|---|
| Amorphous silica | 20 mg |
| Gum base | 800 mg |
| Spray dried peppermint oil | 100 mg |
| Xylitol | 800 mg |
| Sorbitol | 225 mg |
| Magnesium Stearate | 80 mg |
| Stearic Acid | 155 mg |
| Microcrystalline Cellulose | 300 mg |

Example 8

Evidence of Chemotherapeutic Effect with Simultaneous Use of the Peroxide Gum and the Bicarbonate Gum All of the test subjects of Example 6 described a lessening of sensitivity to peroxide when the bicarbonate gums having greater than 10% sodium bicarbonate were chewed together with the peroxide gums. This effect was especially noticeable for the peroxide gums comprising 15% carbamide peroxide. In these gums sodium bicarbonate was present between 250 mg and 400 mg and carbamide peroxide was present between 175 mg and 400 mg. Condition of the gums and breath were observed to have improved, especially for those cases where the patients had inflamed gums at baseline (symptoms typical for gingivitis). The counts of anaerobic and aerobic bacteria decreased dramatically, even after only one 30-minute treatment. These results strongly suggest that the two-composition oral treatment helps remediate symptoms of periodontal diseases, and oral malodor, not only by removing stains and debris from the teeth surface, but also by affecting positive change to the micro-flora inherent to the human oral cavity.

What is claimed is:

1. A teeth-whitening kit comprising a component A separated from a component B, wherein component A is a chewable composition, comprising
an anhydrous chewing gum base having water content of about 1% or less,
an anhydrous fruit acid,
carbamide peroxide having water content of about 2% or less, and
one or more gum additives,
wherein the ratio of gum base:carbamide peroxide:fruit acid, in percent weight relative to the composition, is about 10-50:1-20:0.5-8, and the one or more gum additives are present in an amount sufficient to reach 100% of the weight of the composition; and
wherein component B is a chewable composition, comprising a source of a bicarbonate ion, a gum base, and one or more gum additives, wherein the source of bicarbonate ion and the gum base, respectively, are present in a ratio of about 5-30:15-50 in percent weight relative to the weight of component B, and the one or more gum additives are present in an amount necessary to reach 100% of the weight of component B.

2. The kit of claim 1, wherein the source of bicarbonate ion is sodium bicarbonate.

3. The kit of claim 2, wherein the ratio of fruit acid: carbamide peroxide:sodium bicarbonate, by mass is about 0.5-5:5-20:10-35.

4. The kit of claim 1, wherein component B further comprises a metal carbonate at about 0.001-1% of the weight of component B.

5. The kit of claim 2, wherein the relative amounts of component A and component B per dose of teeth-whitening treatment is such that sodium bicarbonate is present at three times or more relative to the amount of the fruit acid.

6. The kit of claim 1, wherein the fruit acid is citric acid.

7. The kit of claim 1, wherein the relative amounts of component A and component B per dose is such that pH of a water extract of the composition is at least about 7.

8. A teeth-whitening kit comprising a component A separated from a component B, wherein component A is a chewable composition, comprising
an anhydrous chewing gum base having water content of 1% or less,
an anhydrous fruit acid,
carbamide peroxide having water content of 2% or less, and
one or more gum additives,
wherein the ratio of gum base:carbamide peroxide:fruit acid, in percent weight relative to the composition, is 10-50:1-20:0.5-8, and the one or more gum additives are present in an amount sufficient to reach 100% of the weight of the composition; and
wherein component B is a chewable composition, comprising a source of a bicarbonate ion, a gum base, and one or more gum additives, wherein the source of bicarbonate ion and the gum base, respectively, are present in a ratio of 5-30: 15-50 in percent weight relative to the weight of component B, and the one or more gum additives are present in an amount necessary to reach 100% of the weight of component B.

9. The kit of claim 8, wherein the source of bicarbonate ion is sodium bicarbonate.

10. The kit of claim 9, wherein the ratio of fruit acid: carbamide peroxide:sodium bicarbonate, by mass is 0.5-5:5-20:10-35.

11. The kit of claim 8, wherein component B further comprises a metal carbonate at 0.001-1% of the weight of component B.

12. The kit of claim 8, wherein the relative amounts of component A and component B per dose is such that pH of a water extract of the composition is at least 7.

13. The kit of claim 9, wherein the relative amounts of component A and component B per dose of teeth-whitening treatment is such that sodium bicarbonate is present at three times or more relative to the amount of the fruit acid.

14. The kit of claim 8, wherein the fruit acid is citric acid.

15. A teeth-whitening kit comprising a component A separated from a component B, wherein component A is a chewable composition, comprising
an anhydrous chewing gum base having water content of 1% or less,
an anhydrous fruit acid,
carbamide peroxide having water content of 2% or less, and
one or more gum additives,
wherein the ratio of gum base:carbamide peroxide:fruit acid, in percent weight relative to the composition, is 10-50:1-20:0.5-8, and the one or more gum additives are present in an amount sufficient to reach 100% of the weight of the composition; and
wherein component B is a chewable composition, comprising a source of a bicarbonate ion, a gum base, and one or more gum additives, wherein the source of bicarbonate ion and the gum base, respectively, are present in a ratio of 5-30:15-50 in percent weight relative to the weight of component B, and the one or more gum additives are present in an amount necessary to reach 100% of the weight of component B;
wherein component B further comprises a metal carbonate at 0.001-1% of the weight of component B, and the fruit acid is citric acid.

16. The kit of claim 15, wherein the relative amounts of component A and component B per dose is such that pH of a water extract of the composition is at least 7.

* * * * *